US008628868B2

(12) United States Patent
Burns et al.

(10) Patent No.: US 8,628,868 B2
(45) Date of Patent: *Jan. 14, 2014

(54) FLUORINATED POLYTETRAMETHYLENE GLYCOL (PTMG) WITH DIEPOXIDE ENDGROUPS AS MAGNETIC LUBRICANTS

(75) Inventors: John Martin Burns, San Jose, CA (US); Norbert A. Feliss, Aptos, CA (US); Xing-Cai Guo, Tracy, CA (US); Bruno Marchon, Palo Alto, CA (US); Robert Waltman, Gilroy, CA (US)

(73) Assignee: HGST Netherlands B.V., Amsterdam (NL)

( * ) Notice: Subject to any disclaimer, the term of this patent is extended or adjusted under 35 U.S.C. 154(b) by 320 days.

This patent is subject to a terminal disclaimer.

(21) Appl. No.: 13/100,871

(22) Filed: May 4, 2011

(65) Prior Publication Data

US 2012/0282491 A1    Nov. 8, 2012

(51) Int. Cl.
*G11B 5/725* (2006.01)

(52) U.S. Cl.
USPC ......... 428/835.8; 508/582; 508/590; 427/131

(58) Field of Classification Search
None
See application file for complete search history.

(56) References Cited

U.S. PATENT DOCUMENTS

| 4,666,781 | A | 5/1987 | Lehner |
| 4,942,203 | A | 7/1990 | Conti-Ramsden et al. |
| 5,082,714 | A | 1/1992 | Yanai et al. |
| 5,107,033 | A | 4/1992 | Pechhold |
| 5,320,769 | A | 6/1994 | Kinoshita et al. |
| 5,539,059 | A | 7/1996 | Bierschenk et al. |
| 5,663,127 | A | * | 9/1997 | Flynn et al. .................... 508/250 |
| 6,080,486 | A | 6/2000 | Falcone et al. |
| 6,162,521 | A | 12/2000 | Falcone |
| 6,570,041 | B1 | 5/2003 | Kodama et al. |
| 6,579,835 | B2 | 6/2003 | Scicchitano et al. |
| 2005/0037932 | A1* | 2/2005 | Liu et al. ........................ 508/458 |
| 2008/0132664 | A1 | 6/2008 | Shirakawa et al. |
| 2010/0069275 | A1* | 3/2010 | Marchionni et al. .......... 508/582 |
| 2011/0256424 | A1* | 10/2011 | Burns et al. .................... 428/814 |

FOREIGN PATENT DOCUMENTS

| JP | 59-111818 | 6/1984 |
| JP | 2001055440 | 2/2001 |

OTHER PUBLICATIONS

Nikles, et al., "Amine-Quinone Polyurethanes: Preparation of Polyurethane Segmented Block Copolymers Containing 2,5-Bis(N-2-hydroxyethyl-N-methylamino)-1,4-benzoquinone, Toluene Diisocyanate, and an Oligomeric Polyether Diol," Journal of Polymer Science, Part A: Polymer Chemistry, vol. 37, pp. 2339-2345 (1999).
Kim, et al., "Biodegradable Photo-crosslinked Poly(ether-ester) Networks for Lubricious Coatings," Biomaterials, vol. 21, pp. 259-265 (2000).
Ge, et al., "Synthesis and Characterization of a New Fluorinated POlyether Glycol Prepared by Radical Grafting of Hexafluoropropylene onto Polytetramethylene Glycol," European Polymer Journal, vol. 42, pp. 395-401 (2006).

* cited by examiner

*Primary Examiner* — Holly Rickman

(57) ABSTRACT

A surface agent includes two end portions and a middle portion disposed between the end portions. The end portions include a terminal section and a midsection. The terminal section includes at least one surface active functional group. The midsection includes at least one perfluoroethyl ether unit. The middle portion includes at least one perfluorobutyl ether unit.

25 Claims, 3 Drawing Sheets

FLUORINATED POLYTETRAMETHYLENE GLYCOL (PTMG) WITH DIEPOXIDE ENDGROUPS AS MAGNETIC LUBRICANTS

BACKGROUND

1. Field of Disclosure

The invention is generally related to lubricants and, in particular, to derivatives of perfluoropolyether lubricants for magnetic media disks in hard disk drive applications.

2. Description of Related Art

Lubricants, such as boundary lubricants, are used in many types of mechanical devices including disk drives and microelectronic mechanical systems. Such devices typically include a moving part that is lubricated to prevent wear. The moving part moves relative to other parts of the device. Boundary lubricants form a lubricating film when functional groups of the lubricant attach to the surface being lubricated. Boundary lubricants, among other advantages, limit solid-to-solid contact.

In an effort to increase disk drive capacity, industry is seeking to reduce flying height of the slider above the disk. However, lower flying height can induce severe slider/lubricant interactions. For example, slider/lubricant interactions can create moguls, ripples, and depletion in the lubricant on the disk surface. In addition, lubricant can gather on the slider, forming drops that fall onto the disk surface, leaving thick regions. As a result, the thicker regions, moguls, and ripples can cause errors in reading the disk, whereas regions without lubricant may permit surface scratching in the disk or damage to the head of the disk drive. For at least these reasons, lubricants are desired that eliminate or significantly reduce such detriments.

SUMMARY

Derivatives of a perfluoropolyether surface agent and systems incorporating same are disclosed. The surface agent includes segments of perfluoropolyalkyl ether and segments having surface active functional groups. In a particular example, the surface agent includes at least one perfluoropolyalkyl ether segment including perfluorobutyl ether units and at least one perfluoropolyalkyl ether segment including perfluoroethyl ether units. The surface agent may be placed on a media disk comprising a substrate and a magnetic recording layer, and a carbon overcoat layer, with the lubricant on the overcoat layer. In other embodiments, a hard disk drive comprises an enclosure, a disk rotatably mounted to the enclosure and having a substrate with a magnetic recording layer, and an actuator movably mounted to the enclosure and having a head for reading data from the disk, with the surface agent on the disk. The surface agent also may be used on other mechanical devices comprising a movable part subject to wear, with the movable part being lubricated with the surface agent including at least one perfluoropolyalkyl ether segment including perfluorobutyl ether units and at least one perfluoropolyalkyl ether segment including perfluoroethyl ether units.

The foregoing and other objects and advantages of the present invention will be apparent to those skilled in the art, in view of the following detailed description of the present invention, taken in conjunction with the appended claims and the accompanying drawings.

BRIEF DESCRIPTION OF THE DRAWINGS

So that the manner in which the features and advantages of the embodiments are attained and can be understood in more detail, a more particular description of the embodiments briefly summarized above may be had by reference to the appended drawings. However, the drawings illustrate only some embodiments and therefore are not to be considered limiting of the scope of the invention which may admit to other equally effective embodiments.

The use of the same reference symbols in different drawings indicates similar or identical items.

DETAILED DESCRIPTION

Figure 1:
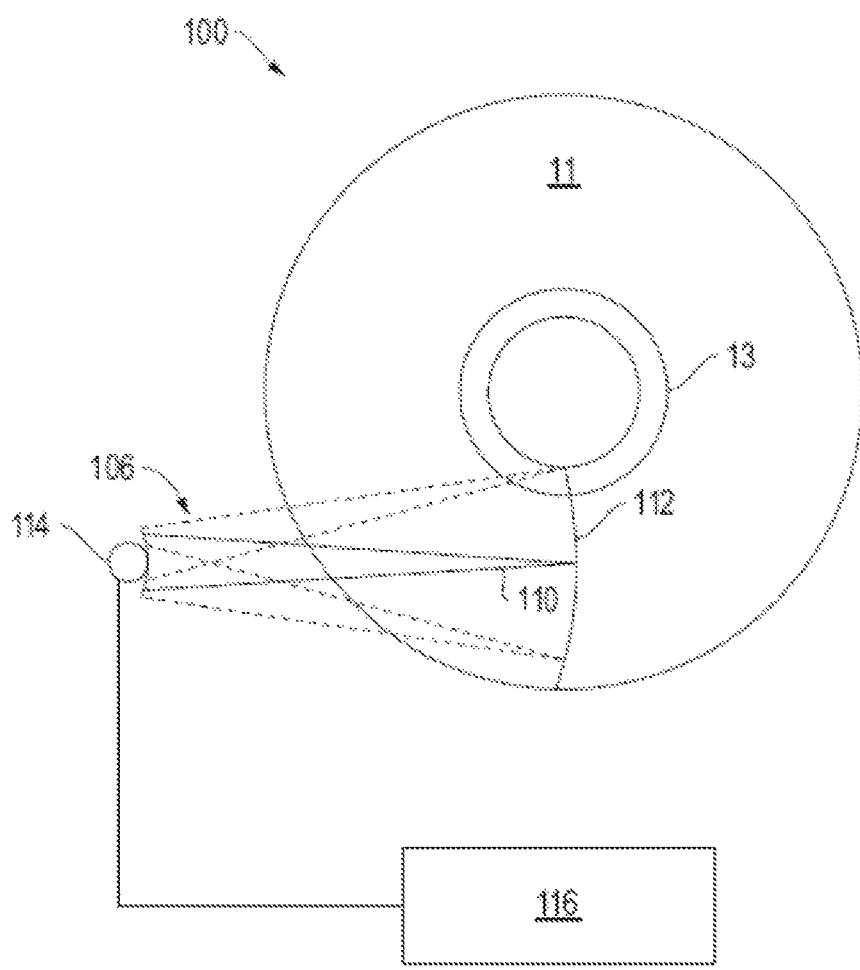
FIG. 1 includes a schematic diagram of one embodiment of a disk drive.

In an exemplary embodiment, a surface agent includes segments of perfluoropolyalkyl ether and segments having surface active functional groups. In a particular example, the surface agent includes at least one perfluoropolyalkyl ether segment including perfluorobutylene-1,4-ether units and at least one separate fluoroalkyl ether segment including fluorobutylene-1,4-ether units. The surface active functional groups include propylene oxide units, 1,2-propyldiol units, or derivatives thereof.

When disposed on a surface, the surface agent may act as a lubricant where the surface active functional groups can bond to the surface and the fluoroalkylether and perfluoropolyalkyl ether segments form a low surface energy region on the surface. In a particular embodiment, the surface can be part of a magnetic storage device.

In an exemplary method, a storage device is formed by dispensing magnetic media having a magnetic surface and applying a surface agent to the magnetic surface. The surface agent may be applied by dip coating, spray coating, spin coating, a vapor deposition technique, or any combination thereof.

As used herein, the terms "portion," "segment," or "section" refer to extents along a backbone or primary chain length of a molecule, typically formed of a chain of carbon and oxygen atoms. Functional groups, such as polar functional groups may extend from carbons bound within the backbone or primary chain of the surface agent molecule.

In an example, the surface agent includes three sections of the formula $R_a$—$R_b$—$R_c$, wherein central section $R_b$ includes a fluorinated polybutylene glycol group of the formula:

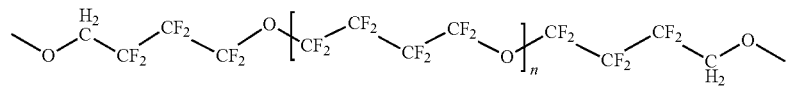

The polybutyl ether section $R_b$ comprises internal octafluorobutyl units flanked by 1,2,3-hexafluorobutyl units. The hexafluorinated butyl units are linked in such a fashion that the non-fluorinated methylene groups of the flanking units are terminally oriented. The internal octafluorobutyl units of the polybutylene ether can be repetitive, i.e. n is at least 1 in the above-depicted formula of $R_b$. In embodiments, n can be in the range of 1 to 6. In another embodiment, n can be in the range of 1 to 3. In another embodiment, n can be 1 or 2.

In yet another embodiment, a lubricant mixture of two surface agents $R_a$—$R_{b1}$—$R_c$ and $R_a$—$R_{b2}$—$R_c$, the two surface agents are distinguished by the value of n. For example, $R_a$—$R_{b1}$—$R_c$ can have n=1 and $R_a$—$R_{b2}$—$R_c$ can have n=2. In another embodiment having a surface agent mixture $R_a$—$R_{b1}$—$R_c$ can have any one value between 1 and 3 and $R_a$—$R_{b2}$—$R_c$ can have any value a different value between 1 and 6.

Further addressing the end units of surface agent, at least one of the end units $R_a$ and $R_c$ is a propylene oxide. The propylene oxide group of the selected from the optically active groups:

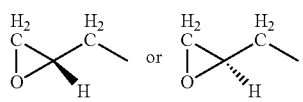

In embodiments, the epoxide moiety of the propylene oxide interacts with the surface onto which the surface agent is applied to. The epoxide moiety can interact with the surface by forces of polarity, such as dipole-dipole or dipole-ion interactions or hydrogen bonds. This type of bonding does not break any bonds in the structure of the surface agents. On the other hand, the epoxide group can bond covalently to the surface, which in turn will break at least one bond in the structure of the surface agent, particularly in the three-membered epoxide ring, as exemplified in the following lubricant surface reaction:

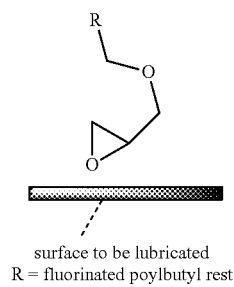

surface to be lubricated
R = fluorinated poylbutyl rest

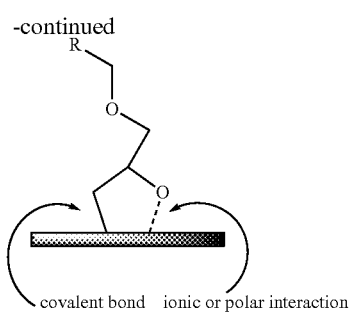

covalent bond   ionic or polar interaction

In embodiments, the surface agent having the formula $R_a$—$R_b$—$R_c$ includes compounds where $R_a$ and $R_c$ are different. $R_a$ can be selected from propylene oxide groups:

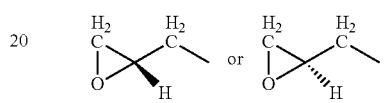

$R_c$ can be selected from 1,2-propyl glycols and 1,2-propyl glycol ethers, such as:

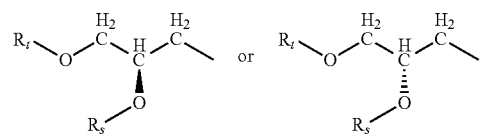

In embodiments, $R_t$ and $R_s$ can be surface active functional groups. In other embodiments, $R_t$ and $R_s$ can be the same or different. In embodiments, $R_t$ and $R_s$ can be selected from hydrogen, hydroxyalkyl, or aminoalkyl. For example, $R_t$ and $R_s$ can be hydroxyl methyl, hydroxyethyl, hydroxyl propyl, hydroxyl butyl, amino methyl, amino ethyl, amino propyl, amino butyl, and any combination thereof.

In further embodiments, the surface agent is selected from the following compounds:

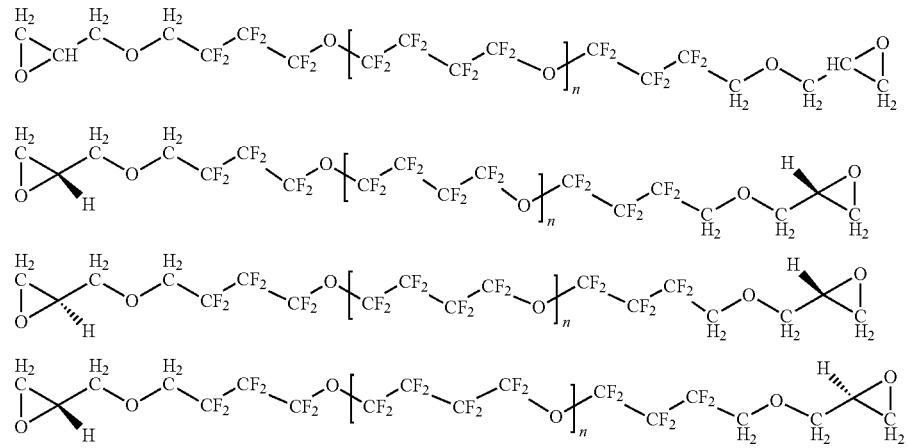

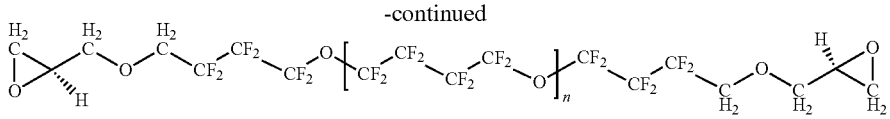

In the above structures, n is at least 1. In embodiments, a mixture of at least two compounds selected from the above structures and n can range from 1 to 6. In other embodiments, n can range from 1 to 3. In yet other embodiments, n can be 1 or 2.

In other embodiments, a lubricant formulation can be a mixture of polyfluorinated glycol ether compounds selected from compounds of the general formula $R_a$—$R_b$—$R_c$, wherein central unit $R_b$, and flanking units $R_a$ and $R_c$ are defined as described herein.

In some embodiments, the lubricant formulation comprises compounds where $R_a$ and $R_b$ are the same and $R_b$ of the compounds varies by the value form.

In one particular embodiment, a lubricant formulation comprises a mixture of at least two surface agents. At least one compound is represented by the structure,

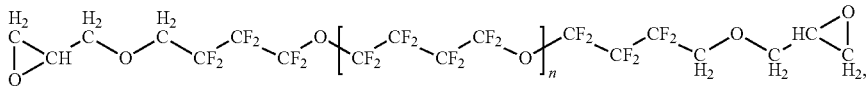

where n=1. At least one second compound is represented by the structure,

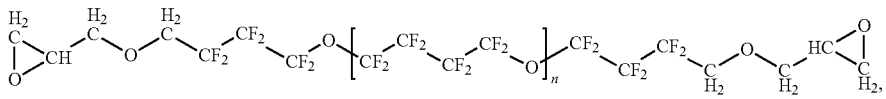

where n=2.

In an exemplary embodiment, the surface agent has an average molecular weight of at least approximately 700 amu. Owing to the nature of the synthesis chemistry, the surface agent may have a distribution of molecular weights. As used herein, the average molecular weight is the weight average molecular weight. In an example, the average molecular weight of the surface agent is in a range of approximately 700 amu to approximately 2000 amu. For example, the average molecular weight may be in a range of approximately 700 amu to approximately 1500 amu, such as a range of approximately 700 amu to approximately 1200 amu, or in a range of approximately 700 amu to approximately 950 amu. In other embodiments, the average molecular weight may be in a range between approximately 750 amu and approximately 850 amu, or even in a range between approximately 800 amu and approximately 825 amu.

In an example, the surface agent can be formed by linking end portions using a middle portion. The end portions may be formed by adding terminal groups on to a perfluoropolyalkyl ether segment. In a particular example, hydroxyl containing segments may be added on to the ends of the perfluoropolyalkyl ether segment, for example, as described in US Patent Application Publication No. 2007/0225183 A1. A middle portion formed of a perfluoropolyalkyl ether segment can be linked between two end portions. For example, the middle portion can be synthesized to include epoxide end groups and reacted with the end portions as described, for example, in U.S. Pat. No. 7,683,012 B2 or Guo et al. "Multidenate functionalized lubricant for ultralow head/disk spacing disk drive," *J. Applied Physics,* 100, 044306 (2006).

Following the synthesis reaction, the surface agent can be separated from other reaction byproducts through fractionation or other separation techniques. As a result, a surface agent having the average molecular weight described above can be obtained.

As described below in Example 1, the surface agent exhibits desirable properties such as Clearance Index, Bonded Ratio, and Durability Index. The Clearance Index, as defined in Example 1, is the difference in thermal flying height control (TFC) clearance relative to the TFC clearance of a ZTMD lubricant described in U.S. Pat. No. 7,683,012 B2. In an example, the Clearance Index of the surface agent is at least 0.7 nm, such as at least 0.5 nm, or even at least 0.3 inn.

The surface agent also exhibits a desirable Bonded Ratio, defined below in Example 1 as the stabilized fraction of bonded molecules remaining after exposure to a solvent as determined by the method of Example 1. For example, the Bond Ratio may be at least 80%, such as at least 85%.

Further, the surface agent exhibits a desirable Durability Index, defined below in Example 1 as the time-to-failure determined by the method described in Example 1. For example, the Durability Index may be at least 4000 seconds, such as at least 2000 seconds, or even at least 1000 seconds.

To facilitate bonding to a surface, the surface agent may be incorporated into a coating solution. For example, the coating solution can include a solvent and the surface agent. The solvent can be a halogenated alkane or a halogenated cycloalkane. In embodiments, the solvent can be a fluorinated alkane or a fluorinated cycloalkane. An exemplary solvent includes a fluorinated solvent (2,3-dihydroperfluoropentane). The coating solution can include at least 0.001 g/l, such as 0.01 g/l of the surface agent, such as at least 0.05 g/l of the surface agent, at least 0.5 g/l of the surface agent, or even at least 1 g/l of the surface agent.

In an example, the surface agent can form a lubricating layer over a component of a storage device. Referring now to FIG. 1, a schematic diagram of an embodiment of a hard disk drive assembly 100 is shown. A hard disk drive assembly 100 generally comprises a housing or enclosure with one or more disks as described herein. The disk comprises magnetic recording media 111, rotated at high speeds by a spindle motor (not shown) during operation. The concentric data tracks 113 are formed on either or both disk surfaces magnetically to receive and store information.

Embodiments of a read or read/write head 110 may be moved across the disk surface by an actuator assembly 106, allowing the head 110 to read or write magnetic data to a particular track 113. The actuator assembly 106 may pivot on a pivot 114. The actuator assembly 106 may form part of a closed loop feedback system, known as servo control, which dynamically positions the read/write head 110 to compensate for thermal expansion of the magnetic recording media 111 as well as vibrations and other disturbances. Also involved in the servo control system is a complex computational algorithm executed by a microprocessor, digital signal processor, or analog signal processor 116 that receives data address information from an associated computer, converts it to a location on the magnetic recording media 111, and moves the read/write head 110 accordingly.

In some embodiments, read/write heads 110 periodically reference servo patterns recorded on the disk to ensure accurate head 110 positioning. Servo patterns may be used to ensure a read/write head 110 follows a particular track accurately, and to control and monitor transition of the head 110 from one track 13 to another. Upon referencing a servo pattern, the read/write head 110 obtains head position information that enables the control circuitry 116 to subsequently realign the head 110 to correct any detected error.

Servo patterns may be contained in engineered servo sectors 112 embedded within a plurality of data tracks 13 to allow frequent sampling of the servo patterns for improved disk drive performance, in some embodiments. In a typical magnetic recording media 111, embedded servo sectors 112 extend substantially radially from the center of the magnetic recording media 11, like spokes from the center of a wheel. Unlike spokes however, servo sectors 112 form a subtle, arc-shaped path calibrated to substantially match the range of motion of the read/write head 110.

In an example, the storage device can be formed by dispensing a component having a magnetic surface and depositing a surface active agent on the magnetic surface. For example, depositing the surface active agent can include dip coating, spin coating, spray coating, a vapor deposition technique, or any combination thereof. In a particular example, the surface agent may form a layer having a thickness in a range of 1 Å to 20 Å, such as a thickness in a range of 6 Å to 12 Å.

EXAMPLE

A surface agent having an approximate structure of formula $R_a$—$R_b$—$R_c$ above is prepared and tested relative to ZTMD lubricant described in U.S. Pat. No. 7,683,012 B2.

A solution of reactants and byproducts formed from linking a middle portion including a perfluoropolybutyl ether segment to end portions including a fluorinated fluorobutylene-1,4-ether segment is fractionated to separate the surface agent from byproducts and unreacted components. Two fractions provide surface agents of desirable molecular weight as indicated by the boiling point of the majority component. These two fractions are blended to provide a surface agent solution, referred to herein as PTMG diepoxide having the structure:

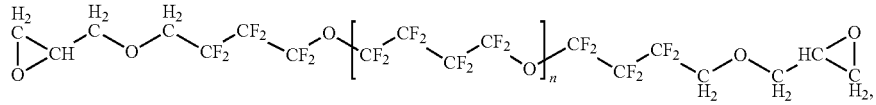

with n being 1 for one fraction and n being 2 for the second fraction.

Figure 2:
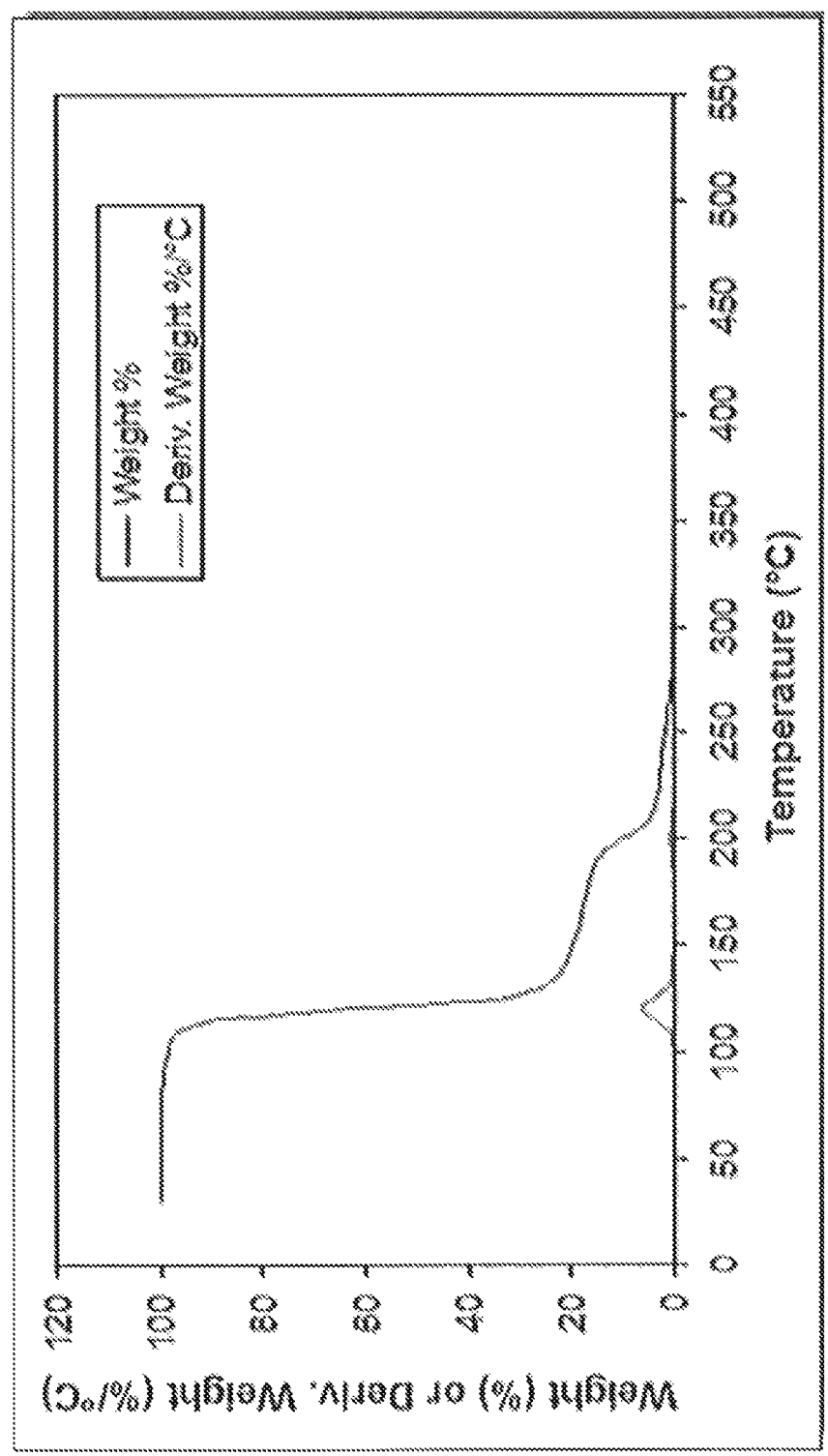
FIG. 2 includes a thermal gravimetric analysis of exemplary surface agents.

FIG. 2 depicts the thermal stability of PTMG diepoxide. The gravimetric shows a stability of more than 90 wt % at a temperature of 100° C. At temperatures above approximately 120° C., degradation of the lubricant takes place leveling off to approximately 20 wt % of the composition remaining on the surface. Another degradation takes place at temperatures approaching 200° C. and all of the applied composition degrades and/or evaporates at temperatures above 250° C. This indicates that the lubricant is thermally stable at the operation temperature (60-70° C.) of hard disk drives.

The surface agent solution is tested in comparison with ZTMD for Bonded Ratio, Clearance Index, and Durability Index. The film thickness is verified using calibrated FTIR analysis. Bonded ratio is the fraction of surface agent remaining on the surface after rinses by solvent such as 2,3-dihydroperfluoropentane.

Figure 3:
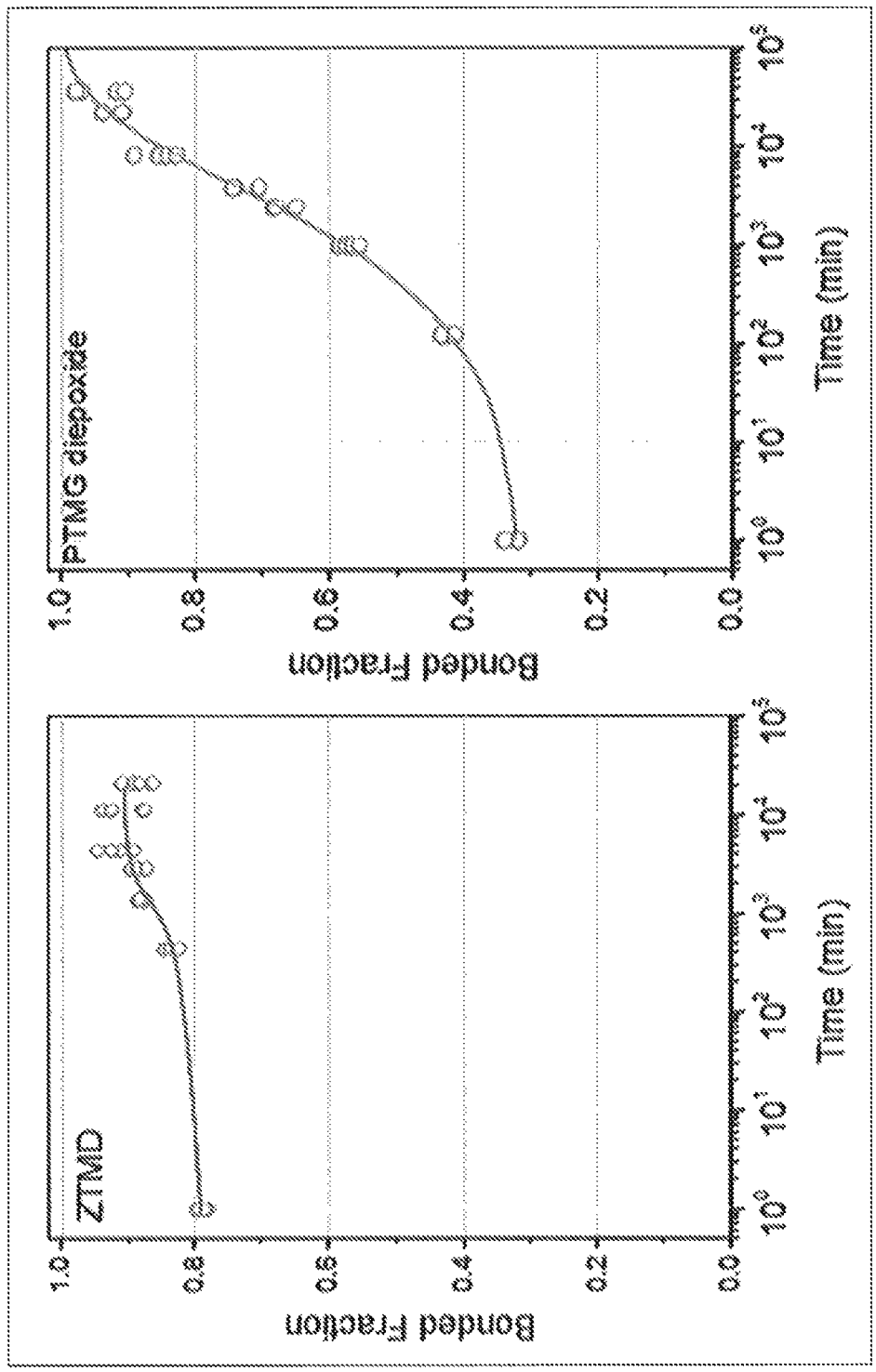
FIG. 3 includes a plot of bonding kinetics for an embodiment of a surface agent.

As illustrated in FIG. 3, the amount of surface agent that remains increases with longer exposure to ambient conditions (20° C. and 50% RH). Advantageously, the initial bonded fraction for PTMG diepoxide is relatively low at approximately 33% bonded, while ZTMD has almost 80% bonding.

It especially advantageous if the initial bonding remains at less than 50% for an extended amount of time, preferably hours. A slow bonding rate allows for sufficient time for final tape polish process where a low bonded ratio is beneficial to reduce damage and increase yield. Fast bonding lubricants do not allow for such measure. As can be seen in FIG. 3, the 50% bonded fraction lies somewhere between 100 and 1000 minutes after application.

Another desired property is that a lubricant reaches high bonding fractions upon completion of the bonding process, preferably within days after lubricating the disk. In this regard for both ZTMD and PTMG diepoxide perform comparable. Over 90% bonding has occurred after 1 to two weeks.

Clearance Index is the difference in measured slider disk clearance relative to ZTMD coated surfaces. Disk clearance is measured in accordance with the method described by Guo et al., "Multidenate functionalized lubricant for ultralow head/disk spacing disk drive," *J. Applied Physics*, 100, 044306 (2006). As illustrated in Table 1, the Clearance Index of PTMG diepoxide is approximately 1.5 nm higher than ZTMD coated surface.

Durability Index is the time until a failure of a head observed during a touchdown stress test. The touchdown stress test is performed by flying a head over the surface of a coated disk. The coated disk includes a coating of one of ZTMD or PTMG diepoxide (both at the same 12 Å thickness). During the test, the head is caused to touchdown at a rate of one touchdown per second through TFC. The length of time until head failure is recorded as the Durability Index. As illustrated in Table 1, ZTMD and 24TMD exhibit similar Durability Index of approximately 4300 seconds.

TABLE 1

| Comparative Performance of ZTMD and PTMG diepoxide | | |
|---|---|---|
| | ZTMD | PTMG diepoxide |
| Clearance Index (nm) | 6.0 | 7.5 |
| Durability Index (sec) | 4326 | 4338 |

As such, embodiments of the surface agent described above advantageously exhibits desirable properties. For example, the surface agent can have a desirable Durability Index and Bond Ratio. Further, the surface agent has a desirable Clearance Index.

This written description uses examples to disclose the embodiments, including the best mode, and also to enable those of ordinary skill in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

We claim:

1. A storage device comprising:
   a component having a magnetic surface; and
   at least one media lubricant disposed on the magnetic surface, the at least one media lubricant selected from the group comprising the formula:

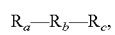

wherein $R_b$ includes

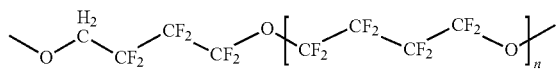

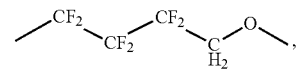

wherein n is at least 1;
   wherein at least one of $R_a$ and $R_c$ is selected from

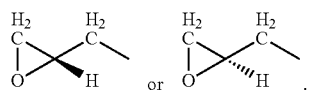

2. The storage device according to claim 1, wherein n is in a range of 1 to 6.

3. The storage device of claim 1, wherein $R_a$ is selected from

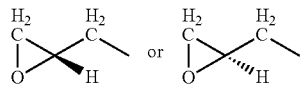

and $R_c$ is selected from

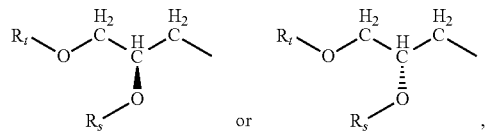

wherein $R_t$ and $R_s$ are the same or different and are selected from H, hydroxyalkyl, or aminoalkyl.

4. The storage device according to claim 1, wherein the at least one media lubricant is selected from

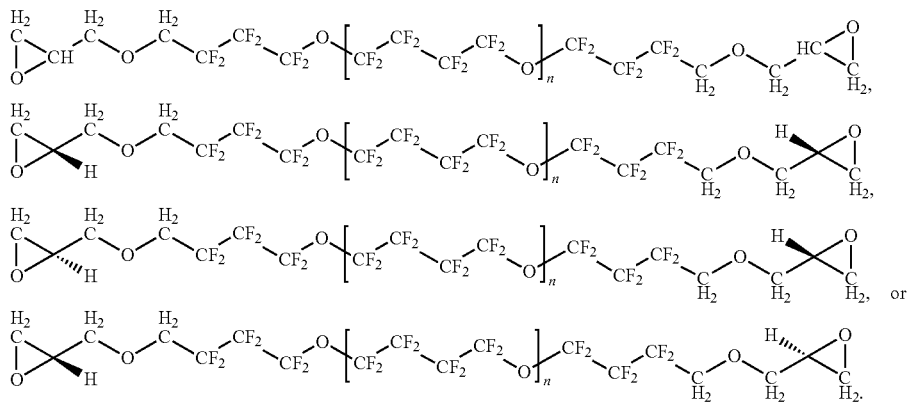

5. The storage device according to claim 4, having a mixture of at least two media lubricants, selected from:

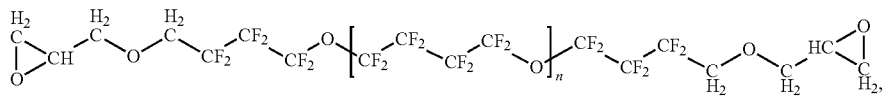

wherein n=1, and

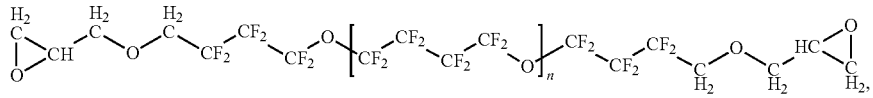

wherein n=2.

6. The storage device of claim 5, wherein the mixture has an average molecular weight between 800 amu and 825 amu.

7. The storage device of claim 1, wherein the media lubricant forms a layer having a thickness in a range of 1 Å to 20 Å.

8. The storage device of claim 7, wherein the media lubricant forms a layer having a thickness in a range of 6 Å to 12 Å.

9. The storage device of claim 1, wherein the media lubricant exhibits a Clearance Index of at least 0.4 nm.

10. The storage device of claim 1, wherein the media lubricant exhibits a Bonded Fraction of at least 80% after one week from deposition on the magnetic surface.

11. The storage device of claim 1, wherein the media lubricant exhibits a Bonded Fraction of less than 50% after one minute from deposition on the magnetic surface.

12. The storage device of claim 1, wherein the media lubricant exhibits a Bonded Fraction of less than 40% after one minute from deposition on the magnetic surface and the Bonded Fraction is at least 80% after one week from deposition on the magnetic surface.

13. The storage device of claim 1, further comprising a reading head disposed to move relative to the magnetic surface.

14. A coating solution comprising:
a solvent; and
at least one surface agent selected from the group comprising the formula:

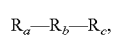

wherein $R_b$ includes

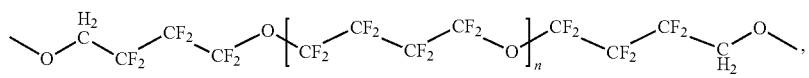

wherein n is at least 1;
wherein at least one of $R_a$ and $R_c$ is selected from

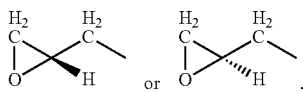

15. The coating solution according to claim 14, wherein the at least one surface agent is selected from

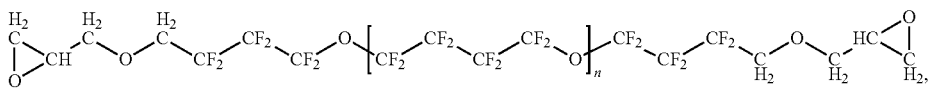

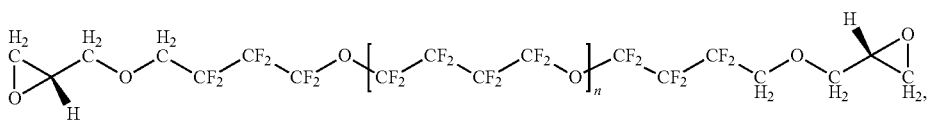

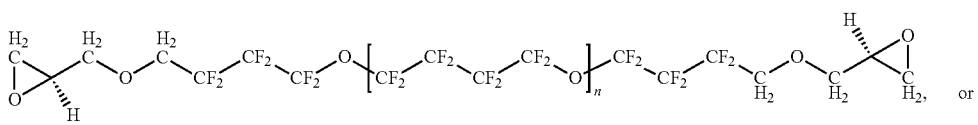

or

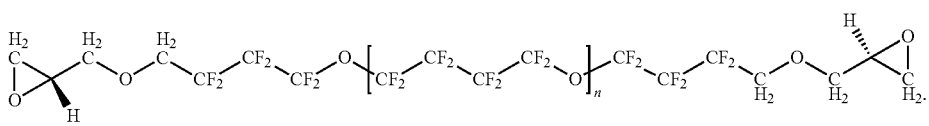

16. The coating solution according to claim 14, having at least two surface agents, selected from:

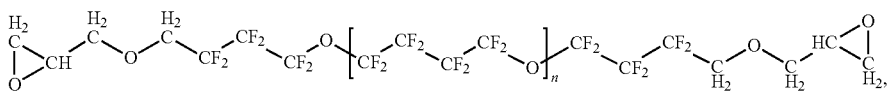

wherein n=1, and

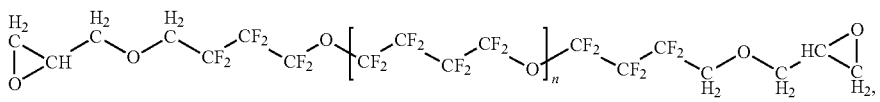

wherein n=2.

17. The coating solution of claim 14 having a concentration of the at least one surface agent of at least 0.001 g/l.

18. The coating solution of claim 14, wherein the solvent comprises a halogenated alkane or a halogenated cycloalkane.

19. The coating solution of claim 18, wherein the solvent comprises a fluorinated alkane or a fluorinated cycloalkane.

20. The coating solution of claim 19, wherein the solvent is 2,3-dihydroperfluoro-pentane.

21. A method of manufacturing a storage device, the method comprising:
dispensing a component having a magnetic surface; and
depositing at least one surface active agent or media lubricant selected from the group comprising the formula:

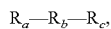

wherein $R_b$ includes

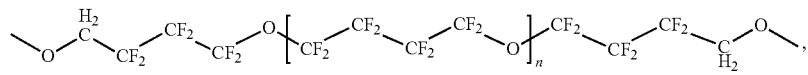

wherein n is at least 1;
wherein at least one of $R_a$ and $R_c$ is selected from

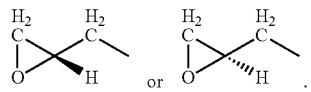

22. The method of claim 21, wherein depositing includes dip coating.
23. The method of claim 21, wherein depositing includes spin coating.
24. The method of claim 21, wherein depositing includes spray coating.
25. The method of claim 21, wherein depositing includes vapor deposition.

* * * * *